United States Patent [19]

Isoda et al.

[11] Patent Number: 4,764,415
[45] Date of Patent: Aug. 16, 1988

[54] ELECTRIC ELEMENT USING OXIDATION-REDUCTION SUBSTANCES

[75] Inventors: Satoru Isoda; Shigetoshi Nara; Satoshi Ueyama; Hiroaki Kawakubo; Akemi Ogura, all of Hyogo, Japan

[73] Assignee: Mitsubishi Denki Kabushiki Kaisha, Tokyo, Japan

[21] Appl. No.: 68,297

[22] Filed: Jul. 1, 1987

[30] Foreign Application Priority Data

| Jul. 1, 1986 [JP] | Japan | 61-155450 |
| Jul. 1, 1986 [JP] | Japan | 61-155446 |
| Jul. 11, 1986 [JP] | Japan | 61-164187 |
| Jul. 11, 1986 [JP] | Japan | 61-164199 |

[51] Int. Cl.$^4$ ................. B32B 9/04; B32B 15/04
[52] U.S. Cl. ................. 428/212; 428/432; 428/459; 428/478.2
[58] Field of Search ............. 428/212, 432, 459, 478.2

[56] References Cited

U.S. PATENT DOCUMENTS

| 3,966,580 | 6/1976 | Janata | 428/478.2 |
| 4,032,901 | 6/1977 | Levinthal | 365/167 |
| 4,103,064 | 7/1978 | McAlear | 428/459 |
| 4,103,073 | 7/1978 | McAlear | 428/459 |
| 4,541,908 | 9/1985 | Niki et al. | 427/414 |
| 4,613,541 | 9/1986 | Isoda | 428/459 |

Primary Examiner—William J. Van Balen
Attorney, Agent, or Firm—Sughrue, Mion, Zinn, Macpeak, and Seas

[57] ABSTRACT

Layers constituting a rectifier or transistor element are respectively formed by oxidation-reduction substances so that a redox potential difference is provided between adjacent layers. The oxidation-reduction substances are selected from biogenic redox protein, pseudo-redox protein and the like. The element is implemented in hyperfine size in molecular level, so that an integrated circuit of super-high density can be attained by using the element.

20 Claims, 4 Drawing Sheets

ELECTRIC ELEMENT USING OXIDATION-REDUCTION SUBSTANCES

BACKGROUND OF THE INVENTION 1. (Field of the Invention)

The present invention relates to a redox electric element, such as a rectifier element or a transistor element, used in the field of integrated circuits, which element is implemented in hyperfine size (of several 10 to several 100 Å) in biomolecular level by using oxidation-reduction substances as material thereof, thereby attaining a high-speed integrated circuit of high density.

2. (Prior Art)

Heretofore, rectifier elements in metal-oxide-semiconductor (MOS) structure as shown in FIG. 1, for example, as described in an article by Yoshihisa Yanai and Yuzuru Nagata, entitled "INTEGRATED CIRCUIT ENGINEERING" (1) have been employed in conventional integrated circuits. In FIG. 1, the reference numeral 11 designates a p-type silicon substrate, the reference numeral 12 designates an n-type region, the reference numeral 13 designates a p-type region, the reference numeral 14 designates an n-type region, the reference numeral 15 designates $SiO_2$ films, and each of the reference numerals 16 and 17 designates an electrode. As shown in FIG. 1, a p-n junction is formed between the electrodes 16 and 17 by the junction of the p-type region 13 and the n-type region 14, thereby attaining rectifying characteristics.

The conventional rectifier elements in the MOS structure can be hyperfinely processed, so that LSIs of 1 M bits employing the rectifier elements in the aforementioned structure or transistor elements in similar structure thereto are now put into practice.

In order to improve such elements in storage capacity and arithmetic speed, the elements themselves must indispensably be in hyperfine structure, whereas mean free paths of electrons are substantially equalized to scales of the elements in hyperfine patterns of about 0.2 $\mu$m in elements using Si and hence the independency of the elements cannot be maintained. Thus, it is anticipated that maturing silicon technology may run into a blank wall in the view of hyperfine structure in the near feature, and hence required is an electric circuit element based on a new principle which can crack the 0.2 $\mu$m barrier.

On the other hand, a plurality of types of biogenic proteins (hereinafter referred to as electron transport proteins) having electron transport functions for carrying electrons in predetermined directions are present in vibo. For example, the electron transport biogenic proteins are embedded in biomembranes in regular orientation, to be in a specific intermolecular arrangement so that electron transport is caused between biomolecules.

The electron transport biogenic proteins show oxidation-reduction (redox) reaction in electron transport in vibo and are capable of making electrons flow from negative redox potential levels of the respective electron transport biogenic proteins to positive redox potential levels. Hence it may be considered that the movement of the electrons can be controlled in molecular level by utilizing such properties of the electron transport proteins. By employing the properties of the electron transport biogenic proteins in vibo, an electronic device has been recently proposed, however, has not yet performed hyperfine structure in size, and not yet attained sufficient rectifying and transistor characteristics.

SUMMARY OF THE INVENTION

According to recent study of the inventors of this invention, it has been recognized that it is possible to form electron transport complexes by combining electron transport biogenic proteins with electron transport organic non-biogenic substances other than the electron transport biogenic proteins present in vibo, or combining only the electron transport organic non-biogenic substances, thereby to provide highly sufficient rectifying and transistor characteristics.

Therefore, an object of the present invention is to provide an electric circuit element, for example, especially a rectifier element or a transistor element, which element is implemented in hyperfine size in biomolecular level by combining oxidation-reduction non-biogenic substances with either electron transport biogenic proteins or organic non-biogenic substances.

In order to achieve the object, it may be considered that two types of electron transport substances (A and B), which are suitably selected to be different in redox potential from each other, can be accumulated in two layers in the form of A-B to thereby form a junction having rectifying characteristics due to the difference in redox potential. An aspect of the present invention is based on this consideration.

Further, it may be considered that such electron transport substances (A and B), which are suitably selected to be different in redox potential from each other, can be accumulated in three layers in the form of A-B-A to thereby form a junction having transistor or switching characteristics due to the difference in redox potential. Another aspect of the present invention is based on this consideration.

A redox electric element in accordance with the first aspect of the present invention comprises a first oxidation-reduction substance film prepared by a first oxidation-reduction substance having a first redox potential; a second oxidation-reduction substance film prepared by a second oxidation-reduction substance having a second redox potential different from the first potential; the second oxidation-reduction substance film being accumulatedly stuck and joined on the first oxidation-reduction substance; first and second electrodes electrically connected to the first and second oxidation-reduction substance films respectively; one of the first and second oxidation-reduction substance films being a film made of selected one of biogenic redox protein and organic non-biogenic substance, the other being a film made of organic non-biogenic substance; a difference between the first and second redox potentials being utilized to provided rectifying characteristics.

In accordance with the second aspect of the present invention, a redox electric element comprises a first oxidation-reduction substance film prepared by a first oxidation-reduction substance having a first redox potential; a second oxidation-reduction substance film prepared by a second oxidation-reduction substance having a second redox potential different from the first potential, the second oxidation-reduction substance film being accumulatedly stuck and joined on the first oxidation-reduction substance; a third oxidation-reduction substance film prepared by a third oxidation-reduction substance having a third redox potential different from the second potential, the third oxidation-reduction substance film being accumulatedly stuck and joined on the second oxidation-reduction substance; first and third electrodes electrically connected to the first and third oxidation-reduction substance films respectively; second electrodes provided to give an electrical influence on the second oxidation-reduction substance film; one of the first, second and third oxidation-reduction substance films being a film made of one of biogenic redox protein and organic non-biogenic substance, one of the other two of the first, second and third oxidation-reduction substance films being a film made of one of biogenic redox protein and organic non-biogenic substance, the remainder one of the first, second and third oxidation-reduction substance films being a film made of organic non-biogenic substance; differences between the first, second and third redox potentials being utilized to provide at least one of transistor and switching characteristics.

DETAILED DESCRIPTION OF THE INVENTION

Figure 1:
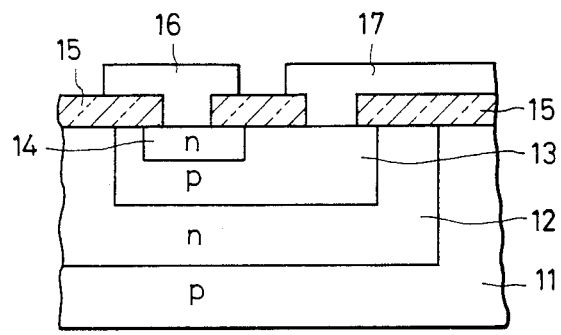
FIG. 1 is a sectional view showing a conventional rectifier element in MOS structure.
Figure 2A:
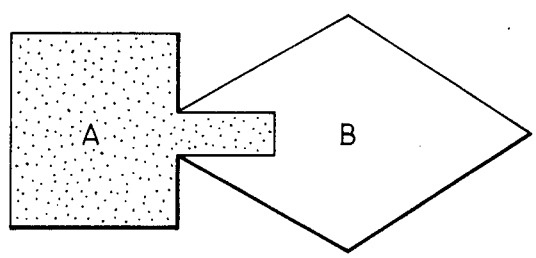
FIG. 2(A) is a typical diagram showing an A-B type oxidation-reduction substance complex.
Figure 2B:
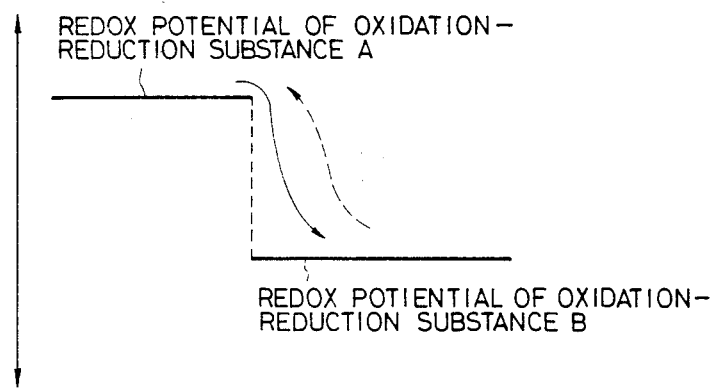
FIG. 2(B) is a diagram showing redox potential states.

In the present invention, rectifying characteristics can be generated by joining at least two types of oxidation-reduction substances having different redox potentials. Referring to FIGS. 2(A) and 2(B) which show a model of an A-B type oxidation-reduction substance complex and the relation in redox potential thereof, the complex prepared by joining two types of oxidation-reduction substances A and B having different redox potentials show rectifying characteristics so that electrons can easily flow from the negative redox potential level to the positive redox potential level in the direction of the solid-line arrow shown in the drawing while the electrons can hardly flow in the reverse direction (of the broken-line arrow in the drawing). By using the complex, it is expected to obtain a rectifier element similar in property to a p-n junction produced by combination of an n-type semiconductor and a p-type semiconductor.

Figure 3A:
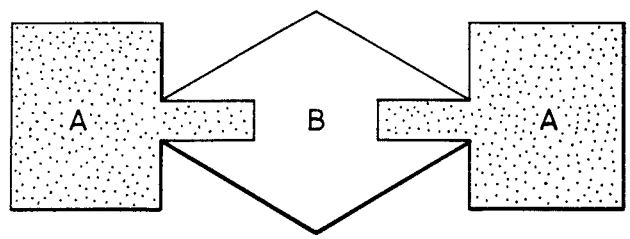
FIG. 3(A) is a typical diagram showing an A-B-A type oxidation-reduction substance complex.
Figure 3B:
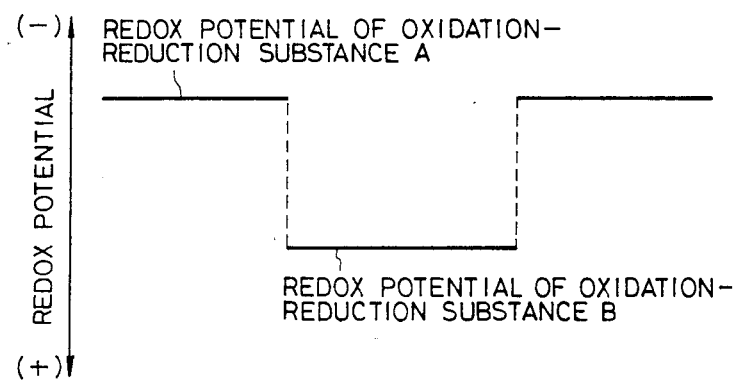
FIG. 3(B) is a diagram showing redox potential states.

In the other aspect of the invention, transistor or switching characteristics can be generated by joining at least two types of oxidation-reduction substances having different redox potentials. Referring to Figs. 3(A) and 3(B), there are shown a model of an A-B-A type oxidation-reduction substance complex and the relation in redox potential thereof. In the complex prepared by joining the oxidation-reduction substances in the form of A-B-A, the redox potential distribution of the three oxidation-reduction substances A, B and A can be changed by controlling a voltage applied to the oxidation-reduction substance B, so that it is expected to obtain an element having transistor or switching characteristics similar to those of a p-n-p junction prepared by combination of an n-type semiconductor and p-type semiconductors.

With respect to the basic technique of the present invention, reference is made to U.S. Pat. No. 4,613,541 (or West German Patent Unexamined Publication DE No. 3600564A1) relating to a prior application by the same assignee of the present application.

Figure 4:
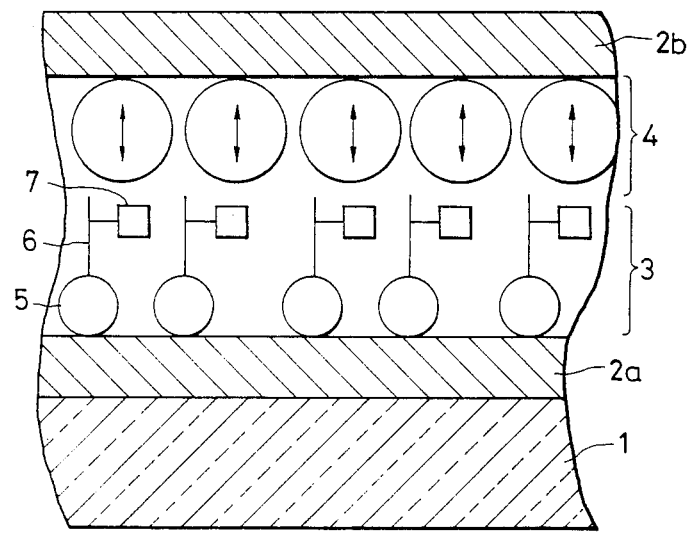
FIG. 4 is a typical sectional view showing a rectifier element according to the first embodiment of the present invention.
Figure 5:
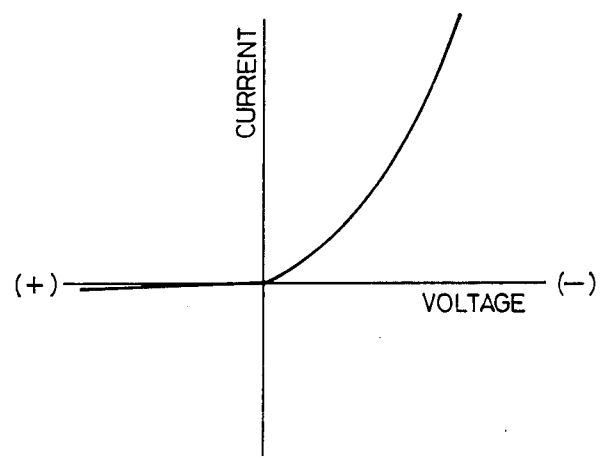
FIG. 5 is a current-voltage characteristic graph of the rectifier element.

An embodiment of the present invention will be described in detail with reference to the accompanying drawings. FIG. 4 is a typical sectional view showing a rectifier element according to a first embodiment of the present invention. In the drawing, the reference numeral 1 designates a substrate, for example, a glass substrate, having insulating characteristics, the reference numerals 2a and 2b respectively designate first and second electrodes, and the reference numerals 3 and 4 respectively designate first and second oxidation-reduction substance films. the second oxidation-reduction substance film 4 is accumulatedly stuck and joined on the first oxidation-reduction substance film 3. In this embodiment, the first oxidation-reduction substance film 3 is a monomolecular film (hereinafter referred as "LB film") of organic synthetic molecules (organic non-biogenic substance) prepared by the Langmuir-Blodgett method. In the drawing, the reference numeral 5 designates hydrophilic groups, the reference numeral 6 designates hydrophobic methylene chains, and the reference numeral 7 designates oxidation-reduction functional group provided with an adequate redox potential. The second oxidation-reduction substance film 4 is predeterminedly oriented in such a manner that electrons can be transported in the protein molecules 4 in a predetermined direction, that is, in a vertical directions with respect to accumulated films(in the direction of the arrow of Fig. 4)while no such electron transfer is caused between the protein molecules in a horizontal direction with respect to accumulated films (that is, in the direction perpendicular to the arrow of FIG. 4). The film 4 is made of biogenic redox protein or pseudo-redox protein as organic non-biogenic substance. For example, in the case where a flavine molecular group is used as oxidation-reduction function group 7 and cytochrome c having the redox potential of +255 mV is used as a redox protein 4, rectifying characteristics as shown in FIG. 5 are obtained.

Figure 6:
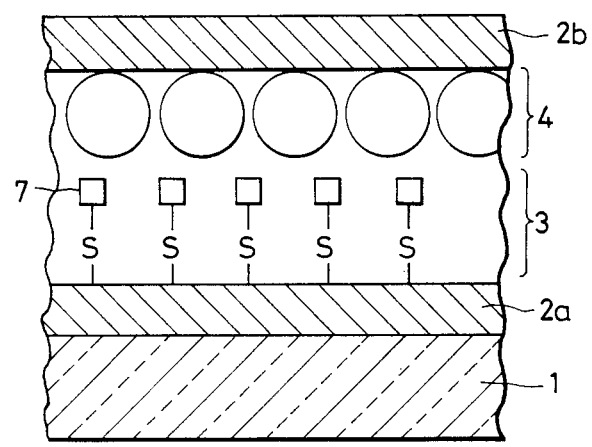
FIG. 6 is a typical sectional view showing a rectifier element according to the second embodiment of the present invention.

FIG. 6 is a typical sectional view showing a rectifier element according to a second embodiment of the present invention. In this embodiment, the first oxidation-reduction substance film 3 is a film (hereinafter referred to as "chemically modified film") prepared by a chemical modification method for chemically modifying electrodes 2a of metal such as Au, Al, Ag, or Pt by organic synthetic molecules (organic non-biogenic substance). The second oxidation-reduction substance film 4 is made of biogenic redox protein or pseudo-redox protein as organic non-biogenic substance. In this embodiment, also rectifying characteristics as shown in FIG. 3 can be obtained as long as the oxidation-reduction function groups 7 and protein 4 are selected adequately.

Accordingly, a rectifier element of hyperfine size in molecular level can be attained by the aforementioned structure, so that an integrated circuit of high density can be attained by using the element.

Although the aforementioned embodiments have shown the case where the first oxidation-reduction substance film 3 is an LB film or a chemically modified film and the second oxidation-reduction substance film 4 is a biogenic redox protein film or a pseudo-redox protein film as an organic non-biogenic substance film, the same effect as in the respective embodiments can be attained in the case where the films are replaced by each other.

Further, such a rectifier element can be attained in the case where both of the first and second oxidation-reduction substance films 3 and 4 are LB films or where one is an LB film and the other is a chemically modified film.

In short, such a rectifier element can be attained under the conditions that first and second oxidation-reduction substance films are different in redox potential from each other and that one of the films is made of either biogenic redox protein or organic non-biogenic substance and the other is made of organic non-biogenic substance.

Figure 7:
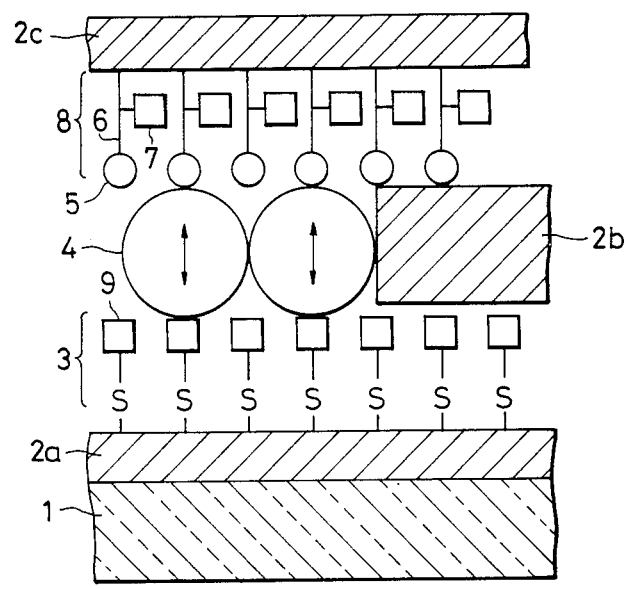
FIG. 7 is an enlarged typical sectional view showing a transistor element according to the third embodiment of the present invention.

FIG. 7 is an enlarged typical sectional view showing a transistor element as a third embodiment according to the present invention. In the drawing, the reference numeral 1 designates an insulating substrate such as that of glass, the reference numerals 2a, 2b and 2c respectively designate first, second and third electrodes, and the reference numerals 3, 4 and 8 respectively designate first, second and third oxidation-reduction substance films. In this embodiment, the first oxidation-reduction substance film 3 is a monomolecular film prepared by chemical modification of metal electrodes 2a by organic synthetic molecules (organic non-biogenic substance). In other words, the film 3 is a chemically modified film. The second oxidation-reduction substance film 4 is a film made of biogenic redox protein or pseudoredox protein as organic non-biogenic substance, which film is oriented in such a manner that electrons can be transported in the protein molecules 4 in a predetermined direction, that is, in a vertical direction with respect to accumulated films (that is, in the direction of the arrow of FIG. 7) while no such electron transfer is caused between the protein molecules in a horizontal direction with respect to accumulated films (that is, in the direction perpendicular to the arrow of FIG. 7). In other words, the film 4 is a protein film. The third oxidation-reduction substance film 8 is a monomolecular film of organic synthetic molecules (organic non-biogenic substance) prepared by the Langmuir-Blodgett method. In other words, the film 8 is an LB film. In the drawing, the reference numeral 5 designates hydrophilic groups, the reference numeral 6 designates hydrophobic methylene chains, and the reference numerals 7 and 9 designate oxidation-reduction functional groups respectively provided with adequate redox potentials.

For example, in the case where flavine molecular groups having the redox potential of about $-200$ mV are used as oxidation-reduction functional groups 7 and 9, and cytochrome c having the redox potential of $+255$ mV is used as a redox protein 4, switching characteristics are attained in the case where voltage is applied to the electrodes 2a, 2b and 2c. Thus, a transistor element can be attained.

The operation and effect of the element will be described in detail with reference to FIGS. 8(a) and 8(b).

Figure 8A:
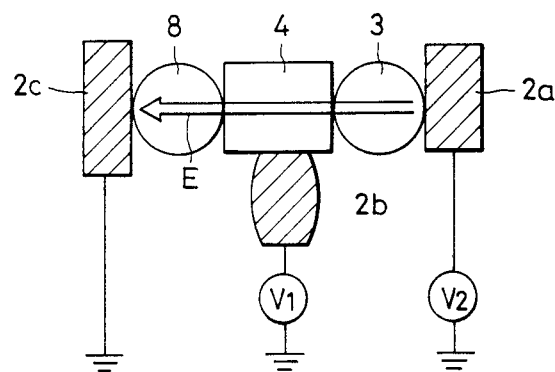
FIG. 8(A) is a typical diagram showing a state where a voltage is applied to the transistor element.
Figure 8B:
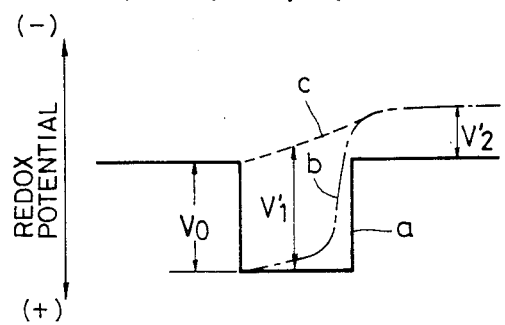
FIG. 8(B) is a diagram showing redox potential states of respective oxidation-reduction substances of the transistor element.

FIG. 8(a) is a typical diagram showing a condition in which a voltage is applied to the transistor element according to the third embodiment of the present invention, and FIG. 8(b) is a diagram showing redox potential states of respective oxidation-reduction substances in this condition. In FIG. 8(b), solid lines indicate redox potential states a before voltages $V_1$ and $V_2$ are applied. Dot-and-dash lines indicate redox potential states (OFF states) b when the voltage $V_1$ is not applied but the voltage $V_2$ is applied as a negative voltage relative to the electrodes 2c. Dot lines indicate redox potential states (ON states) c when the voltage $V_2$ is applied in the similar manner to the states b and the voltage $V_1$ is applied as a negative voltage relative to the electrodes 2c.

In the state b, electrons do not flow between the electrodes 2c and 2a, but in the state c, electrons flow therebetween. That is, a predetermined negative value of the voltage $V_2$ is applied between the electrodes 2c and 2b, the ON-OFF operation of a current between the electrodes 2c and 2b can be controlled by the ON-OFF operation of a predetermined negative value of the voltage $V_1$ between the electrodes 2c and 2b. Thus, switching characteristics can be attained. In the drawing, the symbol $V_0$ denotes a redox potential difference between cytochrome c and flavine molecular groups.

According to this embodiment, a transistor element similar in function to a conventional semiconductor switching element (p-n-p junction type) can be provided as an element of hyperfine size in molecular level, so that a high-speed and high-density integrated circuit can be attained by using the element.

Although the aforementioned third embodiment has shown the case where the first oxidation-reduction substance film 3 is a chemically modified film, the second oxidation-reduction substance film 4 is a biogenic redox protein film or a pseudo-redox protein film as an organic non-biogenic substance film and the third oxidation-reduction substance film 8 is an LB film, it is to be understood that the present invention is not limited to the specific embodiment but various changes in combination can be made as long as one of the first, second and third oxidation-reduction substance films is a biogenic redox protein film or a non-biogenic pseudoredox protein film, one of the other two is an LB film or a chemically modified film, and the remainder one is a biogenic redox protein film, a non-biogenic pseudoredox protein film, an LB film or a chemically modified film.

In short, such a transistor element can be attained under the conditions that first, second and third oxidation-reduction substance films are different in redox potential from each other between adjacent films and that one of the films is a film made of either biogenic redox protein or organic non-biogenic substance, one of the other two is a film made of either biogenic redox protein or organic non-biogenic substance, and the remainder one is a film made of organic non-biogenic substance.

The pseudo-redox protein as organic non-biogenic substance used in the respective aforementioned embodiments may be formed by combination of aminoacid and biogenic redox protein such as cytochrome c or the like or may be formed by combination of biogenic redox protein and amino-acid derivatives produced by substituting F or CH$_3$ for H or by substituting Si or the like for C (Carbon atom).

Further, the pseudo-redox protein may be formed by modifying a biogenic redox protein so as to maintain its active structure and change the other structure.

Examples of the biogenic protein to be modified are non-heme iron-sulfur protein, cytochrome c protein, cytochrome b protein, cytochrome a, flavodoxin, plastocyanine, thioredoxin and the like.

Enzyme may be employed to supply electrons to the biogenic redox protein or the organic non-biogenic pseudoredox protein.

In the Langmuir-Blodgett method, lipid or fatty acid may be previously mixed into the solutions of the biogenic redox proteins or organic non-biogenic pseudoredox proteins dripped on the water surface to form the films to be stuck and joined to the substrate, so that the proteins are adjusted in orientation while the lipid or fatty acid serves to support the protein molecules. Thus, organic thin films are formed between the electrodes and the proteins, so that deterioration of the proteins can be prevented and that excellent electron transfer can be attained.

Although the respective aforementioned embodiments have shown the case where the film made of either biogenic redox protein or organic non-biogenic pseudo-redox protein and the LB film are monomolecular films, the present invention is applicable to the case where the films are monomolecular-film accumulated films. Examples of the biogenic redox protein used for such films are non-heme iron-sulfur protein, cytochrome c protein, cytochrome b protein, cytochrome a, flavodoxin, plastocyanine, thioredoxin and the like.

Examples of the oxidation-reduction function units of organic synthetic molecules (organic non-biogenic substance) used in the LB or chemically modified film are viologen group, flavine group, thionine group, organometallic complex, oxidation-reduction dye, compounds prepared by binding these materials to other organic matters, and the like. Further, examples of the organometallic complex are derivatives of phthalocyanine, derivatives of porphyrin, derivatives of annulene, and the like. Example of the oxidation-reduction dye are methylene blue, methyl capri blue, gallocyanine, indophenol, indigo, pheno-safranine, neutral red, toluidine blue and the like.

Although the embodiment of FIGS. 6 and 7 has shown the case where the chemically modified film employs metal-sulfur bond, it is to be understood that the invention is not limited to the specific embodiment but the film may employ -O-Si- bond in the same manner or the film may be prepared by chemical modification using physical absorption so that modified molecules are not in direct contact with metal electrode surfaces.

As described above, the present invention has the effect that a rectifier or transistor element can be implemented in hyperfine size in molecular level thereby to attain an integrated circuit of high density.

We claim:

1. A redox electric element comprising:
   a first oxidation-reduction substance film prepared by a first oxidation-reduction substance having a first redox potential;
   a second oxidation-reduction substance film prepared by a second oxidation-reduction substance having a second redox potential different from said first potential, said second oxidation-reduction substance film being accumulatedly stuck and joined on said first oxidation-reduction substance;
   first and second electrodes electrically connected to said first and second oxidation-reduction substance films respectively;
   one of said first and second oxidation-reduction substance films being composed of one of biogenic redox protein and organic non-biogenic substance, the other being composed of organic non-biogenic substance;
   a difference between said first and second redox potentials being utilized to provide rectifying characteristics.

2. A redox electric element according to claim 1, wherein said film composed of organic non-biogenic substance is selected from a group consisting of a film composed of pseudo-redox protein, a film composed of organic synthetic molecules prepared by the Langmuir-Blodgett method, and a chemically modified film prepared by a method for chemical modification of a metal electrode by organic synthetic molecules.

3. A redox electric element according to claim 2, wherein said film composed of organic non-biogenic substance comprises one of a monomolecular film and a monomolecular-film accumulated film.

4. A redox electric element according to claim 2, wherein said film composed of one of biogenic redox protein and pseudo-redox protein is oriented in such a manner that electrons are transported in said protein molecules in a vertical direction with respect to accumulated films while no electrons are transported between said protein molecules in a horizontal direction with respect to said accumulated films.

5. A redox electric element according to claim 1, wherein said biogenic redox protein is selected from a group consisting of non-heme iron-sulfur protein cytochrome c protein, cytochrome b protein, cytochrome a, flavodoxin, plastocyanine and thioredoxin.

6. A redox electric element according to claim 2, wherein said organic synthetic molecules have oxidation-reduction functional groups selected from a group consisting of viologen group, flavine group, thionine group, organometallic complex, oxidation-reduction dye, and compounds prepared by binding at least one of said group to other organic materials.

7. A redox electric element according to claim 6, wherein said organometallic complex is selected from a group consisting of derivatives of phthalocyanine, derivatives of porphyrin and derivatives of annulene.

8. A redox electric element according to claim 2, wherein said pseudo-redox protein is prepared by binding one of amino-acid and amino-acid derivative to a redox protein being in nature.

9. A redox electric element according to claim 8, wherein said amino-acid derivative is prepared by substituting one of F and CH$_3$ for H or by substituting Si for C.

10. A redox electric element according to claim 2, wherein supply of electrons to one of said biogenic redox protein and said organic non-biogenic pseudo-redox protein is performed through enzyme.

11. A redox electric element comprising:
    a first oxidation-reduction substance film prepared by a first oxidation-reduction substance having a first redox potential;
    a second oxidation-reduction substance film prepared by a second oxidation-reduction substance having a second redox potential different from said first potential, said second oxidation-reduction substance film being accumulatedly stuck and joined on said first oxidation-reduction substance;

a third oxidation-reduction substance film prepared by a third oxidation-reduction substance having a third redox potential different from said second potential, said third oxidation-reduction substance film being accumulatedly stuck and joined on said second oxidation-reduction substance;

first and third electrodes electrically connected to said first and third oxidation-reduction substance films respectively;

second electrodes provided to give an electrical influence on said second oxidation-reduction substance film;

one of said first, second and third oxidation-reduction substance films being composed of one of biogenic redox protein and organic non-biogenic substance, one of the other two of said first, second and third oxidation-reduction substance films being composed of one of biogenic redox protein and organic non-biogenic substance, the remainder one of said first, second and third oxidation-reduction substance films being composed of organic non-biogenic substance;

differences between said first, second and third redox potentials being utilized to provide at least one of transistor and switching characteristics.

12. A redox electric element according to claim 11, wherein said film composed of organic non-biogenic substance is selected from a group consisting of a film composed of pseudo-redox protein, a film composed of organic synthetic molecules by the Langmuir-Blodgett method, and a chemically modified film by a method for chemical modification of metal electrodes by organic synthetic molecules.

13. A redox electric element according to claim 12, wherein said film composed of organic non-biogenic substance comprising one of a monomolecular film or monomolecular-film accumulated films.

14. A redox electric element according to claim 12, wherein said film composed of one of biogenic redox protein and pseudo-redox protein is oriented in such a manner that electrons are transported in said protein molecules in a vertical direction with respect to accumulated films while no electrons are transported between said protein molecules in a horizontal direction with respect to accumulated films.

15. A redox electric element according to claim 11, wherein said biogenic redox protein is selected from a group consisting of non-heme iron-sulfur protein cytochrome c protein, cytochrome b protein cytochrome a, flavodoxin, plastocyanine and thioredoxin.

16. A redox electric element according to claim 12, wherein said organic synthetic molecules have oxidation-reduction function groups selected from a group consisting of viologen group, flavine group, thionine group, organometallic complex, oxidation-reduction dye, and compounds prepared by binding at least one of said group to other organic materials.

17. A redox electric element according to claim 16, wherein said organometallic complex is selected from a group consisting of derivatives of phthalocyanine, derivatives of porphyrin and derivatives of annulene.

18. A redox electric element according to claim 12, wherein said pseudo-redox protein is prepared by binding one of amino-acid and amino-acid derivative to a redox protein being in nature.

19. A redox electric element according to claim 18, wherein said amino=acid derivative is prepared by substituting one of F and $CH_3$ for H or by substituting Si for C.

20. A redox electric element according to claim 12, wherein supply of electrons to one of said biogenic redox protein and said organic non-biogenic pseudo-redox protein is performed through enzyme.

* * * * *